US011135179B1

(12) United States Patent
Stringham

(10) Patent No.: US 11,135,179 B1
(45) Date of Patent: *Oct. 5, 2021

(54) EYE HEALTH SUPPLEMENT

(71) Applicant: QH Holdings (Oregon), Inc., Eugene, OR (US)

(72) Inventor: James Stringham, Durham, NC (US)

(73) Assignee: QH Holdings (Oregon), Inc., Eugene, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/282,006

(22) Filed: Feb. 21, 2019

Related U.S. Application Data

(60) Provisional application No. 62/786,266, filed on Dec. 28, 2018.

(51) Int. Cl.
| | | |
|---|---|---|
| *A61K 36/00* | (2006.01) | |
| *A61K 31/065* | (2006.01) | |
| *A61K 31/341* | (2006.01) | |
| *A61K 31/355* | (2006.01) | |
| *A61K 33/30* | (2006.01) | |
| *A61K 31/202* | (2006.01) | |
| *A61P 27/02* | (2006.01) | |
| *A61K 35/60* | (2006.01) | |
| *A61K 47/42* | (2017.01) | |
| *A61K 36/28* | (2006.01) | |
| *A61K 35/644* | (2015.01) | |
| *A61K 36/48* | (2006.01) | |

(52) U.S. Cl.
CPC .......... *A61K 31/065* (2013.01); *A61K 31/202* (2013.01); *A61K 31/341* (2013.01); *A61K 31/355* (2013.01); *A61K 33/30* (2013.01); *A61K 35/60* (2013.01); *A61K 35/644* (2013.01); *A61K 36/28* (2013.01); *A61K 36/48* (2013.01); *A61K 47/42* (2013.01); *A61P 27/02* (2018.01)

(58) Field of Classification Search
None
See application file for complete search history.

(56) References Cited

U.S. PATENT DOCUMENTS

| | | |
|---|---|---|
| 5,955,102 A | 9/1999 | Gorenbein et al. |
| 7,887,847 B2 | 2/2011 | Paul, Jr. |
| 9,226,940 B2 | 1/2016 | Roberts |
| 9,889,173 B2 | 2/2018 | Xu et al. |
| 2009/0226547 A1* | 9/2009 | Gilbard ................. A61P 29/00 424/729 |
| 2010/0159029 A1 | 6/2010 | Lang |
| 2010/0330171 A1 | 12/2010 | Gilbard et al. |
| 2012/0258168 A1 | 10/2012 | Montesinos |
| 2013/0195985 A1 | 8/2013 | Lepelletier et al. |
| 2013/0296442 A1 | 11/2013 | Barker et al. |
| 2014/0248369 A1 | 9/2014 | Minatelli et al. |
| 2015/0231192 A1 | 8/2015 | Minatelli et al. |
| 2017/0143646 A1 | 5/2017 | Deshpande et al. |
| 2018/0042894 A1 | 2/2018 | Olmiere et al. |

FOREIGN PATENT DOCUMENTS

| | | |
|---|---|---|
| EP | 2417967 A1 | 2/2012 |
| WO | WO 2014/023082 A1 | 2/2014 |
| WO | WO 2016/151269 A1 | 9/2016 |

OTHER PUBLICATIONS

Chew et al. (2015) JAMA Ophthalmol. 132(2): 142-149, (Year: 2015).*
Koon (2012) Softgels are a Shell game, available at https://www.naturalproductsinsider.com/specialty-nutrients/softgels-are-shell-game. (Year: 2012).*
Brown et al. (1998) Eye 12, 127-133. (Year: 1998).*
"11 Best Lutein, Zeaxanthin, and Meso-Zeaxanthin eye supplements," https://glarminy.com/best-lutein-meso-zeaxanthin-eye-supplements/, 8 pages, accessed Dec. 11, 2017.
Babizhayev, "Glare Disability and Driving Safety," *Ophthalmic Res*; vol. 35, 19-25 (2003).
Bailey, "A new test for the evaluation of disability glare," *Optom Vis Sci* 1991, vol. 68, No. 12, 911-917 (Dec. 1, 1991) (Abstract only).
Digital Blue™ product literature, https://www.quantumhealth.com/shop/product/digital-blue, 2 pages, accessed Dec. 12, 2018.
Eye Promise DVS product literature, 1 page, accessed Dec. 4, 2017.
Fortifeye® Complete Plus product literature, 1 page, accessed Dec. 4, 2017.
Gellermann et al., "In vivo resonant Raman measurement of macular carotenoid pigments in the young and the aging human retina," *J. Opt. Soc. Am. A*; vol. 19, No. 6, 1172-1186 (Jun. 2002).
Haegerstrom-Portnoy et al., "The SKILL Card," *Invest. Ophthalmol Vis Sci*, vol. 38, No. 1, 207-218 (Jan. 1997).
Haegerstrom-Portnoy et al., "Seeing into Old Age: Vision Function Beyond Acuity," *Optometry and Vision Science*; vol. 76, No. 3, 141-158 (Apr. 1999).
Heilusan® eye capsules product literature, https://www.heilusan.de/en/products/produkte/eye-health/eye-capsules/, accessed Jan. 8, 2019, 1-5 pp.
Holistic Complete™ product literature, www.londoneyehospitalpharma.com, 1 page (date unknown).
ICaps Eye Vitamin & Mineral Supplement Softgels product literature, https://www.walgreens.com/store/c/icaps-eye-vitamin-%26-mineral-supplement-softgels/ID . . . , accessed Jan. 8, 2019, 5 pp.
J+D NutraStock™ product literature, www.jdlabs.com, 1 page, accessed Dec. 4, 2017.
Jackson et al., "Aging and dark adaptation," *Vision Research*; vol. 39, 3975-3982 (1999).
Lima et al., "Association of age and macular pigment optical density using dual-wavelength autofluorescence imaging," *Clinical Ophthalmology*; vol. 7, 685-690 (Apr. 3, 2013).

(Continued)

*Primary Examiner* — Russell G Fiebig
(74) *Attorney, Agent, or Firm* — McCoy Russell LLP

(57) ABSTRACT

An eye health supplement and methods of using the eye health supplement are disclosed.

15 Claims, No Drawings

(56) References Cited

OTHER PUBLICATIONS

Lipotriad Visionary AREDS2 Based Eye Vitamin and Mineral Supplement product literature, 1 page, accessed Jan. 8, 2019.
"Lipotriad Visionary Comparison Chart," http://lipotriadvitamins.com/pages/lipotriad-visionary-comparison-chart, 1 page, accessed Dec. 11, 2017.
Macula 30+™ product literature, https://www.quantumhealth.com/shop/product/macula-30, 2 pages, accessed Dec. 12, 2018.
MacuLEH™ product literature, https://londoneyehospitalpharma.com/healthcare-professional-site-our-products/maculeh/, 4 pages, accessed Dec. 4, 2017.
MacuLEH™ product literature, https://www.maculeh.com/maculeh-details.html, accessed Jan. 8, 2019, 7 pp.
"Multivitamins, vision (OTC)," *Medscape*; 3 pages, https://reference.medscape.com/drug/ocuvite-eye-vitamins-mineral-supplements-preservi . . . , accessed Dec. 11, 2017.
"NIH study provides clarity on supplements for protection against blinding eye disease," *National Eye Institute*; 6 pages, https://nei.nih.gov/news/pressreleases/050513, accessed Dec. 11, 2017 (May 5, 2013).
Novahue Vision product literature, http://novahue.com/shop/novahue-vision/, accessed Dec. 4, 2017, 2 pp.
Obana et al., "Effect of age and other factors on macular pigment optical density measured with resonance Raman spectroscopy," *Graefes Arch Clin Exp Ophthalmol*; vol. 252, 1221-1228 (2014).
"Ocular Nutrition Comparison Chart," http://www.i-care.net/compare.html, 4 pages, accessed Dec. 11, 2017.
Owsley, "Vision and Aging," *Annu. Rev. Vis. Sci.*; vol. 2, 255-271 (2016).
PreserVision AREDS 2 Formula product literature, 2 pp., accessed Dec. 4, 2017.
Rozema et al., "Retinal Straylight as a Function of Age and Ocular Biometry in Healthy Eyes," *Investigative Ophthalmology & Visual Science*; vol. 51, No. 5, 2795-2799 (May 2010).
Stringham et al., "Macular carotenoid supplementation improves disability glare performance and dynamics of photostress recovery," *Eye and Vision*; vol. 3, No. 30, 8 pp. (2016).
Stringham et al., "Macular Pigment and Visual Performance Under Glare Conditions," *Optometry and Vision Science*; vol. 85, No. 2, 82-88 (2008).
Stringham et al., "Sufficient Macular Pigment Optical Density for Optimal Visual Performance in Glare Conditions," *Investigative Ophthalmology & Visual Science*; vol. 52, 3638 (Apr. 2011) (Abstract).
Tahir et al., "Slowed dark adaptation in older eyes; effect of location," *Experimental Eye Research*; vol. 155, 47-53 (2017).
Vos, "On the cause of disability glare and its dependence on glare angle, age and ocular pigmentation," *Clin Exp Optom*; vol. 86, No. 6, 363-370 (Nov. 2003).
"What the Age-Related Eye Disease Studies Mean for You," *National Eye Institute*; 6 pages, https://nei.nih.gov/areds2/PatientFAQ, accessed Dec. 12, 2018.
Yeum et al., "Human plasma carotenoid response to the ingestions of controlled diets high in fruits and vegetables," *Am J Clin Nutr*; vol. 64, 594-602 (1996).
Snodderly, D. et al., "The Macular Pigment. I. Absorbance Spectra, Localization, and Discrimination from Other Yellow Pigments in Primate Retinas," Investigative Ophthalmology & Visual Science, vol. 25, No. 6, Jun. 1984, 14 pages.
Seddon, J. et al., "Dietary Carotenoids, Vitamins A, C, and E, and Advanced Age-Related Macular Degeneration," JAMA, vol. 272, No. 18, Nov. 9, 1994, 8 pages.
Hammond, B. et al., "Preservation of Visual Sensitivity of Older Subjects: Association with Macular Pigment Density," Investigative Ophthalmology & Visual Science, vol. 39, No. 2, Feb. 1998, 10 pages.
Age-Related Disease Study Group, "The Age-Related Eye Disease Study (AREDS): Design Implications AREDS Report No. 1," Controlled Clinical Trials, vol. 20, No. 6, Dec. 1999, 28 pages.

"DRI: Dietary Reference Intakes for Vitamin A, Vitamin K, Arsenic, Boron, Chromium, Copper, Iodine, Iron, Manganese, Molybdenum, Nickel, Silicon, Vanadium, and Zinc," National Academy Press, Mar. 2001, 798 pages.
Stringham, J. et al., "Spatial Properties of Photophobia," Investigative Ophthalmology & Visual Science, vol. 45, No. 10, Oct. 2004, 11 pages.
Stringham, J. et al., "The Glare Hypothesis of Macular Pigment Function," Optometry and Vision Science, vol. 84, No. 9, Sep. 2007, 6 pages.
Stringham, J. et al., "Macular Pigment and Visual Performance Under Glare Conditions," Optometry and Vision Science, vol. 85, No. 2, Feb. 2008, 7 pages.
Kris-Etherton, P. et al., "Dietary reference intakes for DHA and EPA," Prostaglandins, Leukotrienes and Essential Fatty Acids, vol. 81, vol. 2-3, Aug. 2009, Available Online Jun. 13, 2009, 6 pages.
Subczynski, W. et al., "Location of macular xanthophylls in the most vulnerable regions of photoreceptor outer-segment membranes," Archive of Biochemistry and Biophysics, vol. 504, No. 1, Dec. 1, 2010, 15 pages.
Stringham, J. et al., "Macular Pigment and Visual Performance in Glare: Benefits for Photostress Recovery, Disability Glare, and Visual Discomfort," Investigative Ophthalmology & Visual Science, vol. 52, No. 10, Sep. 2011, 10 pages.
Querques, G. et al., "Retina and Omega-3," Journal of Nutrition and Metabolism, vol. 2011, No. 748361, Available Online Oct. 31, 2011, 12 pages.
Loskutova, E. et al., "Macular Pigment and Its Contribution to Vision," Nutrients, vol. 5, No. 6, May 29, 2013, 9 pages.
Grahn, B. et al., "Zinc and the eye," Journal of the American College of Nutrition, vol. 20, No. 2 Suppl., May 2001, 5 pages.
Pescosolido, N. et al., "Curcumin: Therapeutical Potential in Ophthalmology," Planta Medica, vol. 80, No. 4, Mar. 2014, Available Online Dec. 9, 2013, 6 pages.
Patryas, L. et al., "The association between dark adaptation and macular pigment optical density in healthy subjects," Graefes Archive for Clinical and Experimental Ophthalmology, vol. 252, No. 4, Apr. 2014, Available Online Jan. 12, 2014, 8 pages.
Ripps, H. et al., "Review: Zinc's functional significance in the vertebrate retina," Molecular Vision, vol. 20, Jul. 31, 2014, 8 pages.
Bovier, E. et al., "A Double-Blind, Placebo-Controlled Study on the Effects of Lutein and Zeaxanthin on Neural Processing Speed and Efficiency," PLoS ONE, vol. 9, No. 9, Sep. 24, 2014, 6 pages.
Hammond, B. et al., "A Double-Blind, Placebo-Controlled Study on the Effects of Lutein and Zeaxanthin on Photostress Recovery, Glare Disability, and Chromatic Contrast," Investigative Ophthalmology & Visual Science, vol. 55, No. 12, Available as Early as Nov. 11, 2014, 7 pages.
Liu, R. et al., "Lutein and Zeaxanthin Supplementation and Association With Visual Function in Age-Related Macular Degeneration," Investigative Ophthalmology & Visual Science, vol. 56, No. 1, Dec. 16, 2014, 7 pages.
Bovier, E. et al., "A randomized placebo-controlled study on the effects of lutein and zeaxanthin on visual processing speed in young healthy subjects," Archives of Biochemistry and Biophysics, vol. 572, Apr. 15, 2015, Available Online Dec. 4, 2014, 4 pages.
Huang, Y. et al., "Effect of Supplemental Lutein and Zeaxanthin on Serum, Macular Pigmentation, and Visual Performance in Patients with Early Age-Related Macular Degeneration," BioMed Research International, vol. 2015, No. 564738, Available Online Mar. 1, 2015, 8 pages.
Stringham, J. et al., "Macular Pigment and Visual Performance in Low-Light Conditions," Investigative Ophthalmology & Visual Science, vol. 56, No. 4, Apr. 2015, 10 pages.
Chew, E. et al., "Effect of Omega-3 Fatty Acids, Lutein/Zeaxanthin, or other Nutrient Supplementation on Cognitive Function: The AREDS2 Randomized Clinical Trial," JAMA, vol. 314, No. 8, Aug. 25, 2015, 24 pages.
Nolan, J. et al., "Enrichment of Macular Pigment Enhances Contrast Sensitivity in Subjects Free of Retinal Disease: Central Retinal Enrichment Supplementation Trials—Report 1," Investigative Ophthalmology & Visual Science, vol. 57, No. 7, Jun. 1, 2016, 11 pages.

(56) References Cited

OTHER PUBLICATIONS

Stringham, J. et al., "Serum and retinal responses to three different doses of macular carotenoids over 12 weeks of supplementation," Experimental Eye Research, vol. 151, Oct. 2016, Available Online Jul. 15, 2016, 8 pages.

Stringham, J. et al., "Macular carotenoid supplementation improves disability glare performance and dynamics of photostress recovery," Eye and Vision, vol. 3, No. 30, Nov. 11, 2016, 8 pages.

Stringham, J. et al., "Contrast Sensitivity and Lateral Inhibition Are Enhanced With Macular Carotenoid Supplementation," Investigative Ophthalmology & Visual Science, vol. 58, No. 4, Apr. 1, 2017, 5 pages.

Stringham, J. et al., "Macular Carotenoid Supplementation Improves Visual Performance, Sleep Quality, and Adverse Physical Symptoms in those with High Screen Time Exposure," Foods, vol. 6, No. 7, Jul. 2017, Available Online Jun. 29, 2017, 13 pages.

Akuffo, K. et al., "The Impact of Supplemental Antioxidants on Visual Function in Nanoadvanced Age-Related Macular Degeneration: A Head-to-Head Randomized Clinical Trail," Investigative Ophthalmology & Visual Science, vol. 58, No. 12, Oct. 1, 2017, 15 pages.

Mohn, E. et al., "Lutein accumulates in subcellular membranes of brain regions in adult rhesus macaques: Relationship to DHA oxidation products," PLoS ONE, vol. 12, No. 10, Oct. 19, 2017, 18 pages.

Korobelnik, J. et al., "Effect of Dietary Supplementation With Lutein, Zeaxanthin, and w-3 on Macular Pigment," JAMA, vol. 135, No. 11, Nov. 2017, Available Online Nov. 9, 2017, 17 pages.

Granger, M. et al., "Dietary Vitamin C in Human Health," Advances in Food and Nutrition Research, vol. 83, Available Online Feb. 16, 2018, 30 pages.

\* cited by examiner

EYE HEALTH SUPPLEMENT

CROSS-REFERENCE TO RELATED APPLICATION

This application claims the benefit of the earlier filing date of U.S. Provisional Application No. 62/786,266, filed Dec. 28, 2018, which is incorporated by reference in its entirety herein.

FIELD

This disclosure concerns embodiments of an eye health supplement dosage form and methods of use.

SUMMARY

Embodiments of an eye health supplement dosage form and methods of using the eye health supplement dosage form are disclosed.

In some embodiments, the eye health supplement dosage form includes 1 part by weight zeaxanthin, 1-20 parts by weight lutein, 10-45 parts by weight vitamin C, 5-115 parts by weight vitamin E, 0.5-10 parts by weight zinc, and 10-200 parts by weight omega-3 oils providing 5-100 parts by weight docosahexaenoic acid (DHA) and 5-100 parts by weight eicosapentaenoic acid (EPA). In certain embodiments, the eye health supplement dosage form includes 1.5-6 mg zeaxanthin, 7.5-30 mg lutein, 62.5-250 mg vitamin C, 42-168 mg vitamin E, 3.75-15 mg zinc; and 75-300 mg omega-3 oils comprising 37.5-150 mg DHA and 37.5-150 mg EPA.

In any of the above embodiments, the eye health supplement dosage form may further include fish oil, gelatin, glycerin, sunflower oil, yellow beeswax, water, carob, or any combination thereof. In some embodiments, the eye health supplement dosage form consists essentially of zeaxanthin, lutein, vitamin C, vitamin E, zinc, DHA, EPA, fish oil, gelatin, glycerin, sunflower oil, yellow beeswax, water, and carob. In some embodiments, the eye health supplement dosage form consists essentially of, or consists of, 3 mg zeaxanthin, 15 mg lutein, 125 mg vitamin C, 84 mg vitamin E, 7.5 mg zinc, 75 mg DHA, 75 mg EPA, fish oil, glycerin, sunflower oil, yellow beeswax, water, and carob.

In any of the above embodiments, the zinc may be provided by zinc gluconate. In any of the above embodiments, the eye health supplement dosage form may not comprise resveratrol. In some embodiments, the eye health supplement dosage form is a softgel.

In some embodiments, a method of supporting eye health includes administering to a subject a dose of an eye health supplement dosage form as disclosed herein, wherein the dose is effective to support eye health. Administering may be performed daily.

In some embodiments, the dose comprises 250 mg vitamin C, 168 mg vitamin E, 15 mg zinc, 30 mg lutein, 6 mg zeaxanthin, 150 mg DHA, and 150 mg EPA. In certain embodiments, administering comprises orally administering two eye health supplement dosage forms to the subject, each eye health supplement dosage form comprising 3 mg zeaxanthin, 15 mg lutein, 125 mg vitamin C, 84 mg vitamin E, 7.5 mg zinc, 75 mg DHA, and 75 mg EPA.

In any of the above embodiments, supporting eye health may comprise supporting a healthy macula, supporting visual performance; or a combination thereof. Supporting a health macula may include supporting a macular density of at least 0.60 over a period of time. Supporting visual performance may include one or more of, or all of, (i) supporting visual performance in low light conditions, (ii) supporting the ability of the subject's eyes to recover from glare, (iii) supporting contrast sensitivity, (iv) reducing eye strain, and/or v) reducing eye fatigue.

DETAILED DESCRIPTION

A healthy retina, including the macula, is an important part of the eye for vision throughout life. The retina, including the macula, is constantly under stress. As they age, many people develop significant problems that impact their vision.

Embodiments of the disclosed eye health supplement dosage form, when administered to a subject, support eye health. In some embodiments, the eye health supplement dosage form supports a healthy macula and/or visual performance. For example, embodiments of the eye health supplement dosage form may support normal macular density (e.g., a normal pigment density, e.g., lutein and zeaxanthin pigment density), support visual performance in low light conditions, and/or support the ability of the subject's eyes to recover from glare.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise. In addition, the term "and/or" when used in this document is to be construed to include the conjunctive "and", the disjunctive "or", and both "and" and "or". Also, the terms "includes" and "has" have the same meaning as "comprises" and the terms "including" and "having" have the same meaning as "comprising".

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components as used in the specification or claims are to be understood as encompassing variations up to ±5% relative to the stated value. When the disclosure states "substantially equal to," the following value encompasses variations up to ±2% relative to the stated value. When the disclosure states "equal to," the following value encompasses variations up to ±1% relative to the stated value.

Although there are alternatives for various components, parameters, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 2016 (ISBN 978-1-118-13515-0).

In order to facilitate review of the various embodiments of the disclosure, the following explanations of specific terms are provided:

Administering: Administration by any route to a subject (e.g., a human). As used herein, administration typically but not necessarily refers to oral administration.

Consisting essentially of: The term "consisting essentially of" means that the eye health supplement does not contain any active components other than those recited, and contains no more than trace amounts (e.g., <1 wt %) of additional non-active components.

Consisting of: The term "consisting of" excludes all components not specified except for impurities ordinarily associated therewith.

Dosage form: A form suitable for administration to a subject, e.g., a softgel, tablet, capsule, or the like. The dosage forms of the claims can be broken up into sub-dosage form which together comprise or consist essentially of the components that add up to the dosage form.

Effective dose: An amount sufficient to provide and/or support a beneficial effect to a subject or a given percentage of subjects.

Omega-3 oil: A polyunsaturated fatty acid characterized by a double bond three atoms away from the terminal methyl group. The three primary omega-3 oils in human physiology are α-linolenic acid (ALA), eicosapentaenoic acid (EPA), and docosahexaenoic acid (DHA). ALA is found in plant oils. EPA and DHA are commonly found in marine oils and are obtained from fish, fish oils, squid oils, and krill oil.

Softgel: An oral dosage form, typically comprising a gelatin-based shell surrounding a liquid fill.

Subject: As used herein, the term "subject" refers to a mammal, particularly a human.

Vitamin C: The term vitamin C, as used herein, is synonymous with ascorbic acid.

Vitamin E: The term vitamin E, as used herein, is synonymous with d-alpha tocopherol. Vitamin E may be measured in milligrams or international units (IU), where 1 IU is the biological equivalent of 0.67 mg d-alpha tocopherol.

II. EYE HEALTH SUPPLEMENT DOSAGE FORM

Embodiments of the disclosed eye health supplement dosage form include zeaxanthin, lutein, vitamin C, vitamin E, zinc, and omega-3 oils, the omega-3 oils providing docosaheaenoic acid (DHA) and eicosapentaenoic acid (EPA). The zinc may be provided by zinc gluconate. In some embodiments, the eye health supplement dosage form does not comprise resveratrol.

In any of the above embodiments, the eye health supplement dosage form may comprise 1 part by weight zeaxanthin, 1-20 parts by weight lutein, 10-45 parts by weight vitamin C, 5-115 parts by weight vitamin E, 0.5-10 parts by weight zinc, and 10-200 parts by weight omega-3 oils providing 5-100 parts by weight DHA and 5-100 parts by weight EPA. In one embodiment, the eye health supplement dosage form comprises 1 part by weight zeaxanthin, 1-10 parts by weight lutein, 20-60 parts by weight vitamin C, 20-40 parts by weight vitamin E, 2-3 parts by weight zinc, and 20-80 parts by weight omega 3 oils providing 10-40 parts by weight DHA and 10-40 parts by weight EPA. In another embodiment, the eye health supplement dosage form comprises 1 part zeaxanthin, 3-7 parts by weight lutein, 35-45 parts by weight vitamin C, 25-35 parts by weight vitamin E, 2-3 parts by weight zinc, and 40-60 parts by weight omega-3 oils providing 20-30 parts by weight DHA and 20-30 parts by weight EPA. In still another embodiment, the eye health supplement dosage form comprises 1 part by weight zeaxanthin, 5 parts by weight lutein, 41.7 parts by weight vitamin C, 28 parts by weight vitamin E, 2.5 parts by weight zinc; and 50 parts by weight omega-3 oils providing 25 parts by weight DHA and 25 parts by weight EPA. In yet another embodiment, the eye health supplement dosage form comprises the following components in amounts substantially equal to, or equal to, 1 part by weight zeaxanthin, 5 parts by weight lutein, 41.7 parts by weight vitamin C, 28 parts by weight vitamin E, 2.5 parts by weight zinc; and 50 parts by weight omega-3 oils providing 25 parts by weight DHA and 25 parts by weight EPA.

In any of the above embodiments, the eye health supplement dosage form may comprise 1.5-6 mg zeaxanthin, 7.5-30 mg lutein, 62.5-250 mg vitamin C, 42-168 mg vitamin E, 3.75-15 mg zinc, and 75-300 mg omega-3 oils comprising 37.5-150 mg DHA and 37.5-150 mg EPA. In one embodiment, the eye health supplement dosage form comprises 2-4 mg zeaxanthin, 10-20 mg lutein, 100-150 mg vitamin C, 75-100 mg vitamin E, 5-10 mg zinc, and 100-200 mg omega-3 oils providing 50-100 mg DHA and 50-100 mg EPA. In another embodiment, the eye health supplement dosage form comprises 3 mg zeaxanthin, 15 mg lutein, 125 mg vitamin C, 84 mg vitamin E, 7.5 mg zinc, 75 mg DHA, and 75 mg EPA. In some examples, the amounts are substantially equal to, or equal to, 3 mg zeaxanthin, 15 mg lutein, 125 mg vitamin C, 84 mg vitamin E, 7.5 mg zinc, 75 mg DHA, and 75 mg EPA.

In any of the above embodiments, the eye health supplement dosage form may further comprise fish oil, gelatin, glycerin, sunflower oil, yellow beeswax, water, carob, or any combination thereof. In some embodiments, the eye health supplement dosage form consists essentially of, or consists of, zeaxanthin, lutein, vitamin C, vitamin E, zinc, DHA, EPA, fish oil, glycerin, sunflower oil, yellow beeswax, water, and carob. In certain embodiments, the eye health supplement dosage form consists essentially of, or consists of, 3 mg zeaxanthin, 15 mg lutein, 125 mg vitamin C, 84 mg vitamin E, 7.5 mg zinc, 75 mg DHA, 75 mg EPA, fish oil, glycerin, sunflower oil, yellow beeswax, water, and carob. In certain embodiments, the eye health supplement dosage form consists essentially of, or consists of, the following components in amounts substantially equal to, or equal to, 3 mg zeaxanthin, 15 mg lutein, 125 mg vitamin C, 84 mg vitamin E, 7.5 mg zinc, 75 mg DHA, 75 mg EPA, plus fish oil, glycerin, sunflower oil, yellow beeswax, water, and carob.

In any of the foregoing embodiments, the zinc may be provided by zinc gluconate. In any of the foregoing embodiments, the lutein may be present as free lutein. In some embodiments, the lutein and zeaxanthin are provided by Lutemax 2020® marigold extract (OmniActive Health Technologies, Morristown, N.J.), an extract providing lutein and both zeaxanthin isomers (R,R and R,S [meso]-zeaxanthin) at a 5:1 ratio by mass.

In any of the foregoing embodiments, the dosage form may be a softgel, a capsule (e.g., a sealed hard capsule), or a tablet. In some embodiments, the dosage form is a softgel. Softgels typically comprise a gelatin-based shell surrounding a liquid fill. Thus, in some embodiments, the dosage form comprises a gelatin-based shell surrounding a liquid fill comprising, consisting essentially of, or consisting of zeaxanthin, lutein, vitamin C, vitamin E, zinc, DHA, EPA, fish oil, glycerin, sunflower oil, yellow beeswax, water, and carob. The gelatin-based shell may comprise gelatin, water, a plasticizer, and optionally an opacifier and/or a colorant.

III. METHODS OF USE

Embodiments of a method for supporting eye health comprise administering to a subject a dose of an eye health supplement dosage form as disclosed herein, wherein the dose is effective to support eye health. In some embodiments, the effective dose comprises 3-12 mg zeaxanthin, 15-60 mg lutein, 125-500 mg vitamin C, 80-340 mg vitamin E, 7.5-30 mg zinc, and 150-600 mg omega-3 oils comprising 75-300 mg DHA and 75-300 mg EPA. In one embodiment, the effective dose comprises 5-7 mg zeaxanthin, 25-35 mg lutein, 200-300 mg vitamin C, 125-200 mg vitamin E, 10-20 mg zinc, and 200-400 mg omega-3 oils providing 100-200 mg DHA and 100-200 mg EPA. In another embodiment, the effective dose comprises 6 mg zeaxanthin, 30 mg lutein, 250 mg vitamin C, 168 mg vitamin E, 15 mg zinc, 150 mg DHA, and 150 mg EPA. In another embodiment, the effective dose comprises the following components in amounts substantially equal to, or equal to, 6 mg zeaxanthin, 30 mg lutein, 250 mg vitamin C, 168 mg vitamin E, 15 mg zinc, 150 mg DHA, and 150 mg EPA. In any of the foregoing embodiments, the zinc may be provided by zinc gluconate.

Administration may be by any suitable route, although in most instances the dosage form is orally administered. In some embodiments, the dose is administered daily. The dose may be administered once daily, or the dose may be broken into two or more sub-doses administered throughout the day. For example, one half of the dose may be administered at a first time and the second half of the dose may be administered at a subsequent time.

In some embodiments, each dosage form includes less than the effective dose, and more than one dosage form can be taken by the subject. For example, in certain embodiments, each dosage form includes half of the effective dosage, and the subject takes two dosage forms in a day. In such embodiments, each eye health supplement dosage form comprises 1.5-6 mg zeaxanthin, 7.5-30 mg lutein, 62.5-250 mg vitamin C, 42-168 mg vitamin E, 3.75-15 mg zinc, and 75-300 mg omega-3 oils comprising 37.5-150 mg DHA and 37.5-150 mg EPA. In certain embodiments, each eye health supplement dosage form comprises 3 mg zeaxanthin, 15 mg lutein, 125 mg vitamin C, 84 mg vitamin E, 7.5 mg zinc, 75 mg DHA, and 75 mg EPA. In certain embodiments, administering comprises orally administering two eye health supplement dosage forms to the subject, each eye health supplement dosage form comprising 3 mg zeaxanthin, 15 mg lutein, 125 mg vitamin C, 84 mg vitamin E, 7.5 mg zinc, 75 mg DHA, and 75 mg EPA. In some examples, the amounts are substantially equal to, or equal to, 3 mg zeaxanthin, 15 mg lutein, 125 mg vitamin C, 84 mg vitamin E, 7.5 mg zinc, 75 mg DHA, and 75 mg EPA. In any of the foregoing embodiments, the zinc may be provided by zinc gluconate.

Zeaxanthin and lutein can be obtained from dietary sources, such as dark-green leafy vegetables, eggs, carrots, sweet potatoes, dried fruit, citrus fruit, green peas, green beans, romaine lettuce, Brussel sprouts, bell peppers, grapes, squash, and corn. However, zeaxanthin and lutein supplementation has been shown to exhibit a beneficial effect on ocular health, particularly as a subject ages. Zeaxanthin and lutein are present in the macula and supplementation may support or even increase macular pigment optical density and/or promote enhanced visual health and performance, which is indicative of good retinal health. A third carotenoid, meso-zeaxanthin is a non-dietary carotenoid that is also present in the macula. Meso-zeaxanthin is produced in the retina from lutein by isomerization. Zeaxanthin and lutein supplementation also been shown to increase visual processing speed as macular pigment density is augmented. Zeaxanthin and lutein supplementation also has been shown to improve visual recovery from glare and to improve visual performance in low light. These features may be attributed at least in part to the spectral properties of zeaxanthin and lutein, which absorb short-wavelength (blue) light (e.g., light having a wavelength within a range of 380-550 nm). Additionally, zeaxanthin and lutein supplementation has been correlated with a reduced risk of age-related macular degeneration (AMD).

Omega-3 oils, particularly DHA and EPA, enhance the bioavailability of lutein and zeaxanthin, as well as the bioavailability of vitamin E. DHA also provides essential structural components of the retina. Vitamin E, DHA, and lutein have been shown to work in concert by aggregating together in neural membranes, and interacting to promote healthy tissue and function.

Vitamin C is an antioxidant that has been demonstrated to support retinal metabolism and vascular protection. Zinc plays a role in maintaining normal ocular function, and is present in high concentrations in ocular tissue, particularly in the retina and choroid.

Researchers with the Age-Related Eye Disease Study (AREDS) reported in 2001 that a formulation including 500 mg vitamin C, 400 international units of vitamin E, 15 mg beta-carotene, 80 mg zinc as zinc oxide, and 2 mg copper as cupric oxide could reduce the risk of developing advanced age-related macular degeneration (AMD). In 2006, the original AREDS formulation was modified to omit beta-carotene, and add 10 mg lutein, 2 mg zeaxanthin, and 1000 mg of omega-3 fatty acids (350 mg DHA and 650 mg EPA. The revised formulation is known as AREDS2.

In some embodiments, a dose of the eye health supplement dosage form disclosed herein includes greater amounts of zeaxanthin and/or lutein than a dose of the AREDS2 formulation. For example, where a dose of the AREDS2 formulation includes 2 mg zeaxanthin and 10 mg lutein, a dose of the disclosed eye health supplement dosage form may include 6 mg zeaxanthin and 30 mg lutein, thereby providing superior results in supporting eye health. The superior results may be more pronounced in older subjects, such as subjects over the age of 30, over the age of 40 over the age of 50, or over the age of 60. Older subjects may experience reduced bioavailability of zeaxanthin and/or lutein from supplements, resulting in decreased absorption in the subject's serum and/or eye.

In some embodiments, administering to a subject a dose of an eye health supplement dosage form as disclosed herein supports eye health. Supporting eye health may comprise supporting a healthy macula, supporting visual performance, or a combination thereof.

Supporting a healthy macula includes supporting macular density over a period of time, such as a period of several days, weeks, months, or even years. Macular density refers to macular pigment density. Macular pigment is a pigmented spot in the center of the retina. The macular pigment comprises lutein and zeaxanthin. The macular pigment protects the macula from harmful blue light and helps maintain macular function. The thickness or density of the macular pigment varies amongst individuals and can change over time. In particular, macular density may decrease as a subject ages. Low macular density is a known risk factor for AMD. A low macular density also may reduce visual processing speed. Studies have shown that macular density also is related to glare disability and photostress recovery (Stringham et al., *Optom Vis Sci* 2008, 85:82-88). Macular pigment optical density (MPOD) may be measured, for example, using dual wavelength autofluorescence imaging, scanning laser ophthalmoscopy, resonance Raman spectroscopy, or heterochromatic flicker photometry technology. The MPOD score is based on a scale from 0 to 1. A low MPOD score may be defined as a score of from 0-0.2, a mid-range is an MPOD score from 0.21-0.44, and an MPOD score greater than 0.45 is considered to be a high density. A score below 0.45 indicates an increased risk of developing AMD. Based on visual performance data, an MPOD of at least 0.60 is desirable (Stringham et al., *ARVO Meeting Abstracts* Apr. 22, 2011, 52:3638). Some studies have shown that MPOD may peak at 45-50 years of age, followed by a gradual decrease as a subject ages, particular after the age of 60 (see, e.g., Lima et al., Clinical *Ophthalmology* 2013, 7:685-690). Stringham et al. demonstrated that MPOD may be increased with lutein and zeaxanthin supplementation (Stringham et al., *Optom Vis Sci* 2008, 85:82-88).

Supporting visual performance comprises one or more of, or all of, (i) supporting visual performance in low-light conditions, (ii) supporting the ability of the subject's eyes to recover from glare, (iii) supporting contrast sensitivity, (iv) reducing eye strain, and/or (v) reducing eye fatigue. Even in the absence of ocular disease, many older adults have difficulty seeing under low illumination including a loss of steady-state light sensitivity and a delay in rod-mediated dark adaptation; older adults also may experience delayed glare recovery (see, e.g., Owsley, *Annu Rev Vis Sci* 2016, 2:255-271; Babizhayev, *Ophthalmic Res* 2003, 35:19-25; Haegerstrom-Portnoy et al., *Optometry and Vis Sci* 1999, 76(3):141-158). Low luminance visual acuity may be assessed, for example, with a SKILL card (Haegerstrom-Portnoy et al., *Invest. Ophthalmol Vis Sci* 1997, 38:207-218). Glare recovery may be assessed, for example, having a subject view the glare source of the Berkley Glare test (Bailey, *Optom Vis Sci* 1991, 68:911-917) for one minute, followed by assessing visual acuity based on the time required for the subject to read the line two lines larger than the subject's previously assessed SKILL dark chart acuity (Haegerstrom-Portnoy et al., *Optometry and Vis Sci* 1999, 76(3):141-158). Photostress, or glare, recovery also may be assessed with an 8 cycle/degree, 15% contrast Gabor patch target after each of five successive exposures to intense LED lights (Stringham et al., *Eye and Vision* 2016 3:30). Stringham et al. demonstrated that MPOD may be increased with lutein and zeaxanthin supplementation, with concomitant improvements in disability glare threshold and photostress recovery (Stringham et al., *Optom Vis Sci* 2008, 85:82-88; Stringham et al., *Eye and Vision* 2016 3:30).

In some embodiments, administering to a subject a dose of an eye health supplement dosage form as disclosed herein, particularly when the subject is administered doses of the eye health supplement dosage form over a period of time, supports a macular density of >0.45, such as a macular density of at least 0.50 or at least 0.60. For example, the macular density may remain substantially stable (e.g., varying by less than 10% relative to an initial macular pigment density) over a period of days, weeks, months, or years, or may decrease at a slower rate compared to the macular density of a subject that has not been administered the eye health supplement dosage form or compared to a rate of macular density decrease in the subject prior to receiving the eye health supplement dosage form.

In some embodiments, administering to a subject a dose of an eye health supplement dosage form as disclosed herein, particularly when the subject is administered doses of the eye health supplement dosage form over a period of time, supports visual performance. A subject receiving doses of the eye health supplement dosage form, particularly over a period of several days, weeks, months, or years, may experience greater and/or more stable visual performance, as evidenced by increased visual acuity and/or decreased eye discomfort, in low-light conditions such as in dimly-lit areas or at nighttime, relative to the subject's visual performance prior to receiving the eye health supplement dosage form or compared to a similar subject (e.g., similar age, same gender, similar general health) did not receive the eye health supplement dosage form. Alternatively, the subject's visual performance in low-light conditions may show greater stability over a period of days, weeks, months, or years, compared to a similar subject who did not receive the eye health supplement dosage form or relative to the subject's own visual performance prior to receiving the eye health supplement dosage form. A subject receiving doses of the eye health supplement dosage form, particularly over a period of several days, weeks, months, or years, also may report an increased ability of the eyes to recover from glare, such as glare attributable to blue light, relative to the subject's ability to recover from glare prior to receiving the eye health supplement dosage form.

Advantageously, the increased amounts of zeaxanthin and lutein present in the disclosed eye health supplement dosage forms relative to the AREDS2 formulation may provide faster and/or enhanced benefits to the subject, such as a more stable macular pigment density, a greater increase in macular pigment density, a more stable visual performance in low-light conditions, an improved visual performance in low-light conditions, a more stable ability to recover from glare, and/or an increased ability to recover from glare, compared to a similar subject that receives the AREDS2 formulation or to a similar subject that does not receive an eye health supplement. The subject also may experience a more stable or increased macular pigment density and/or a more stable or improved visual performance relative to the subject's own macular pigment density and/or visual performance prior to receiving one or more doses of the disclosed eye health supplement dosage forms.

IV. METHODS OF MAKING

Methods of making softgel, hard capsule, and tablet dosage forms are known in the art. Processes for making softgel capsule shells, hard capsules, and tablets are known. See, e.g., Aulton, M., *Aulton's Pharmaceutics: The Design & Manufacture of Medicines*, 527-533 (Kevin M G Taylor, Ed., 3rd Ed., 2001). In some embodiments, the dosage form is a softgel made by a rotary die process involving continuous formation of a heat seal between two ribbons of gelatin to form a soft capsule shell while simultaneously filling the shell with a fill formulation. The gelatin composition for the shell may further include a plasticizer (e.g., glycerol, sorbitol, propylene glycol, or the like) and/or a colorant. In certain embodiments, the process of making the softgel may further include applying a coating to the softgel. For example, an enteric coating may be applied to a softgel as is known to those skilled in the art.

Typically, the fill formulation is a liquid at the manufacturing temperature. The fill formulation comprises zeaxanthin, lutein, vitamin C, vitamin E, zinc, and omega-3 oils, the omega-3 oils providing docosaheaenoic acid (DHA) and eicosapentaenoic acid (EPA). In some embodiments, the fill formulation comprises, consists essentially of, or consists of, zeaxanthin, lutein, vitamin C, vitamin E, zinc, omega-3 oils comprising DHA and EPA, fish oil, glycerin, sunflower oil, yellow beeswax, water, and carob.

V. EXAMPLES

Example 1

Effects of Macular Xanthophyll Supplementation on Macular Pigment Optical Density Because of the potential for diminished bioavailability with age, effects on serum and retinal concentrations of lutein and zeaxanthin (collectively termed "macular xanthophylls [MXans]) after supplementation with both low (12 mg) and relatively high (36 mg) doses of MXans will be investigated in both young (18-25 yrs.) and older (>50 yrs.) subjects.

Methods: Young (e.g., 18-25 yrs.) and older (e.g., >50 yrs), healthy subjects will be recruited into a 6-month, double-blind, placebo-controlled trial to evaluate the effects of MXan supplementation. Subjects will be randomly assigned to one of three groups: placebo, 12 mg/day, or 36 mg/day total MXans; all measures will be taken at baseline and 6 months. MXan concentration in the retina (termed macular pigment optical density [MPOD]) will be measured via customized heterochromatic flicker photometry. Serum MXan concentrations will be quantified via colorimetric microplate assay, and high-performance liquid chromatography, respectively.

Results: Based on the properties of the MXans and reduced bioavailability with age for these nutrients, it is expected that, although consistent daily supplementation will significantly increase MPOD, the dose-response relationship will not be linear for older adults, and that the higher dose (36 mg/day) will lead to more robust responses in both serum and retina.

Example 2

Effects of Supplementation with MXans in Combination with Vitamin C, Vitamin E, Zinc, DHA, and EPA on Disability Glare Performance and Dynamics of Photostress Recovery The macular xanthophylls (MXans) lutein, zeaxanthin, and mesozeaxanthin comprise the diet-derived macular pigment (MP). The purpose of this study is to determine effects of daily MXan supplementation, in combination with vitamin C, vitamin E, zinc, DHA, and EPA on the optical density of MP (MPOD), and visual performance in glare, including repeated-exposure photostress recovery (PSR), and disability glare (DG) thresholds in healthy subjects older than 50 years.

Methods: This study will be a double-blind, placebo-controlled trial. Volunteers (e.g., volunteers aged>50 yrs.), will be recruited to participate in this study. Subjects will supplement daily their diet with either a supplement (each dose of two softgels comprising 250 mg vitamin C, 168 mg vitamin E, 15 mg zinc, 30 mg lutein, 6 mg zeaxanthin, 150 mg DHA, and 150 mg EPA), hereinafter called the "Formulation Supplement" or placebo for 6 months. The Formulation Supplement may also be compared to one or more other commercially available formulations. MPOD will be assessed with customized heterochromatic flicker photometry. PSR times for an 8 cycle/degree, 15% contrast Gabor patch target will be determined after each of five successive exposures to intense LED lights. DG threshold, meant to simulate the effect of bright oncoming headlights at night, will be defined as the intensity of a ring of lights through which subjects were able to maintain visibility of the aforementioned target. Measures of all parameters will be conducted at baseline and 6 months. Repeated-measures ANOVA, and Pearson product-moment correlations will be used to determine statistically significant correlations, and changes within and between groups.

Results: Based on previous studies of effects of supplementation with MXans on visual performance in glare, it is expected that MPOD for subjects in the supplementation group receiving the Formulation Supplement will be increased significantly versus placebo. Additionally, it is expected that PSR times and DG thresholds will be improved significantly from baseline compared to placebo. Specifically, PSR times are expected to increase by at least 40%, and exhibit less fatigue with repeated exposures. For DG thresholds, an improvement in tolerance performance of at least 30% light intensity is expected. Lastly, it is expected that PSR thresholds and DG thresholds will be significantly correlated with each other, indicating an overall effect of improvement of vision in glare.

Example 3

Effects of Lutein and Zeaxanthin Supplementation on Contrast Sensitivity

Once deposited in the retina, the macular carotenoids lutein (L) and zeaxanthin (Z) have been shown to enhance several parameters of visual performance. One of these parameters, contrast sensitivity, has no apparent physical basis. This study will investigate whether increasing macular pigment optical density (MPOD, via L+Z supplementation) could enhance lateral inhibitory processes, and thereby improve contrast sensitivity (CS).

Methods. Sixty young (18-25 years), healthy individuals will be recruited to participate in a 6-month, double-masked, placebo-controlled study. Those randomly assigned to the treatment group will ingest daily two pills containing a total of 36 mg L+Z. Effects on MPOD will be assessed via heterochromatic flicker photometry. Lateral inhibition sensitivity (LIS) will be determined with a computer-based, user-adjustable Hermann grid. Contrast sensitivity (at 8 cycles/degree) will be determined with a two-alternative, forced-choice procedure.

Results. Based on previous observations of these phenomena, coupled with published reports in animal models on the effects of reduced oxidative stress leading to enhanced neurophysiology in the retina, it is expected that MPOD, LIS, and CS will increase significantly in treatment groups between baseline and 6 months, versus placebo. It is also expected that there will be direct relationships determined between the changes in MPOD and both LIS and CS, such that a demonstrable link can be established and cause and effect may be addressed.

In view of the many possible embodiments to which the principles of the disclosed invention may be applied, it should be recognized that the illustrated embodiments, as described in the claims, which form a portion of this disclosure, are only desirable examples of the invention and should not be taken as limiting the scope of the invention.

Rather, the scope of the invention is defined by the following claims, which are incorporated into this specification and form a portion of this disclosure. I therefore claim as my invention all that comes within the scope and spirit of these claims.

I claim:

1. An eye health supplement dosage form, comprising:
   4-6 mg zeaxanthin;
   15-30 mg lutein;
   62.5-250 mg vitamin C;
   42-168 mg vitamin E;
   3.75-15 mg zinc;
   carob; and
   75-300 mg omega-3 oils providing 37.5-150 mg docosahexaenoic acid (DHA) and 37.5-150 mg eicosapentaenoic acid (EPA),
   wherein the zinc is provided by zinc gluconate.

2. The eye health supplement dosage form of claim 1, wherein the eye health supplement dosage form does not comprise resveratrol.

3. The eye health supplement dosage form of claim 1, comprising:
   1 part by weight zeaxanthin;
   5 parts by weight lutein;
   41.7 parts by weight vitamin C;
   28 parts by weight vitamin E;
   2.5 parts by weight zinc; and
   50 parts by weight omega-3 oils providing 25 parts by weight DHA and 25 parts by weight EPA.

4. The eye health supplement dosage form of claim 1, further comprising fish oil, gelatin, glycerin, sunflower oil, yellow beeswax, water, carob, or any combination thereof.

5. The eye health supplement dosage form of claim 4, consisting essentially of zeaxanthin, lutein, vitamin C, vitamin E, zinc, DHA, EPA, fish oil, gelatin, glycerin, sunflower oil, yellow beeswax, water, and carob.

6. The eye health supplement dosage form of claim 1, consisting essentially of:
   at least 6 mg zeaxanthin;
   at least 30 mg lutein;
   125 mg vitamin C;
   84 mg vitamin E;
   7.5 mg zinc;
   75 mg DHA;
   75 mg EPA;
   fish oil;
   gelatin;
   glycerin;
   sunflower oil;
   yellow beeswax;
   water; and
   carob.

7. The eye health supplement dosage form of claim 1, wherein the lutein is present as free lutein.

8. The eye health supplement dosage form of claim 1, wherein the dosage form is a softgel.

9. A method of supporting eye health, comprising administering to a subject a dose of an eye health supplement dosage form according to claim 1, wherein the dose is effective to support eye health.

10. The method of claim 9, wherein administering is performed daily.

11. The method of claim 9, wherein the dose comprises 250 mg vitamin C, 168 mg vitamin E, 15 mg zinc, 30 mg lutein, 6 mg zeaxanthin, 150 mg DHA, and 150 mg EPA.

12. The method of claim 11, wherein the amounts are substantially equal to 250 mg vitamin C, 168 mg vitamin E, 15 mg zinc, 30 mg lutein, 6 mg zeaxanthin, 150 mg DHA, and 150 mg EPA.

13. The method of claim 9, wherein administering comprises orally administering two eye health supplement dosage forms to the subject, each eye health supplement dosage form comprising 3 mg zeaxanthin, 15 mg lutein, 125 mg vitamin C, 84 mg vitamin E, 7.5 mg zinc, 75 mg DHA, and 75 mg EPA.

14. The method of claim 13, wherein the amounts are substantially equal to 3 mg zeaxanthin, 15 mg lutein, 125 mg vitamin C, 84 mg vitamin E, 7.5 mg zinc, 75 mg DHA, and 75 mg EPA.

15. The method of claim 9, wherein supporting eye health comprises supporting a healthy macula, supporting visual performance; or a combination thereof.

* * * * *